United States Patent [19]
Clarembeau

[11] Patent Number: 5,877,375
[45] Date of Patent: Mar. 2, 1999

[54] PRODUCTION OF MONOOLEFIN OLIGOMER

[75] Inventor: Michel Clarembeau, Temploux, Belgium

[73] Assignee: Amoco Corporation, Chicago, Ill.

[21] Appl. No.: 659,661

[22] Filed: Jun. 6, 1996

[30] Foreign Application Priority Data

Jun. 12, 1995 [EP] European Pat. Off. ............ 95250138

[51] Int. Cl.⁶ ...................................... C07C 2/08
[52] U.S. Cl. ................ 585/510; 585/502; 585/506; 585/508; 585/521; 585/525
[58] Field of Search .................. 585/502, 506, 585/508, 510, 525, 521

[56] References Cited

U.S. PATENT DOCUMENTS

| | | | |
|---|---|---|---|
| 3,382,291 | 5/1968 | Brennan | 585/521 |
| 3,780,128 | 12/1973 | Shubkin | 585/525 |
| 3,997,621 | 12/1976 | Brennan | 585/525 |
| 4,045,508 | 8/1977 | Cupples et al. | 585/511 |
| 4,225,739 | 9/1980 | Nipe et al. | 585/525 |
| 4,239,930 | 12/1980 | Allphin et al. | 585/525 |
| 4,409,415 | 10/1983 | Morganson et al. | 585/521 |
| 4,434,309 | 2/1984 | Larkin et al. | 585/525 |
| 4,436,947 | 3/1984 | Morganson et al. | 585/510 |
| 4,902,846 | 2/1990 | DiLeo et al. | 585/510 |
| 4,910,355 | 3/1990 | Shubkin et al. | 585/510 |
| 4,956,512 | 9/1990 | Nissfolk et al. | 585/525 |
| 4,956,513 | 9/1990 | Walker et al. | 585/525 |
| 5,068,487 | 11/1991 | Theriot | 585/525 |
| 5,095,172 | 3/1992 | Lanier et al. | 585/510 |
| 5,396,013 | 3/1995 | Theriot | 585/510 |
| 5,420,373 | 5/1995 | Hope et al. | 585/525 |

FOREIGN PATENT DOCUMENTS

| | | | |
|---|---|---|---|
| 0497206 | 8/1992 | European Pat. Off. | 585/525 |

*Primary Examiner*—Walter D. Griffin
*Attorney, Agent, or Firm*—Joseph DiSalvo; James R. Henes; Stephen L. Hensley

[57] ABSTRACT

A monoolefin oligomerization process which gives high yields of dimer and trimer at high monoolefin conversions in a single stage reaction is described. The process involves contacting a $C_{6-20}$ vinyl olefin with a catalyst comprising boron trifluoride and from 0.075 to 0.5 mol %, based on the total quantity of monoolefin being used, of an alcohol catalyst promoter. The oligomerization is performed at a temperature below about 40° C. and under a pressurized atmosphere of boron trifluoride in the range of 2 to 4 bars gauge until the monoolefin conversion is at least 95% and the combined total of dimer and trimer in the liquid reaction mixture is at least 60% by weight.

8 Claims, No Drawings

PRODUCTION OF MONOOLEFIN OLIGOMER

BACKGROUND

It is known to produce monoolefin oligomers by use of boron trifluoride as the catalyst together with a co-catalyst component. A variety of co-catalysts have been proposed for this use including water, alcohols, ethers, esters, aldehydes, ketones, and acid anhydrides. Oligomers produced in this manner are useful in the production of synthetic lubricating oils of different viscosities. Typically the production of such products, often referred to as PAOs, involves oligomer fractionation, hydrogenation and back blending to achieve desired properties. Usually the dimers and trimers, especially those of 1-decene, are of greatest utility in the production of low viscosity PAOs for various end use applications.

U.S. Pat. No. 4,045,507 to Cupples, et al. describes a multi-stage process for oligomerizing 1-decene which includes use of a series of two or more tank type reactors. The patentees found that the trimer to tetramer ratio decreases with increasing 1-decene conversion in both stages of a two-stage operation, and that this ratio is higher in the second and succeeding reactors. Thus the process described in the patent operates at low conversion in the first stage and at higher conversions in succeeding stages of the process. The patent shows in Examples 5 and 6 of Table I that at 1-decene conversions of 83.4% and 90.5% the amount of dimer in the product was only 5.2% and 3.8%, respectively. In addition, the combined total of dimer and trimer in the products was 47.8% and 83.4% conversion and 38.9% at 90.5% conversion.

THE INVENTION

In accordance with this invention the oligomerization only requires a single stage reaction using one reactor. In addition, although operated at high 1-olefin conversions (significantly higher than described in the foregoing patent), the oligomerization process of this invention gives substantially higher yields of dimer and trimer than the yields achieved in the patent at high conversions. Moreover, by operating at high conversions the amount of unreacted monomer in the present process is reduced as compared to the process of the patent. And all of these advantages are accomplished while at he same time reducing costs associated with the overall operation.

Provided by this invention is a monoolefin oligomerization process which comprises contacting a linear a-monoolefin having in the range of 6 to 20 carbon atoms per molecule with a catalyst comprising boron trifluoride and n the range of from 0.1 to 0.5 mol %, based on the mols of monoolefin used, f an alcohol catalyst promoter, at an oligomerization temperature of 20°–40° C. and under a pressurized atmosphere of boron trifluoride in the range of 2 to 4 bars gauge until the monoolefin conversion is at least 95% and the combined total of dimer and trimer in the liquid reaction mixture is at least 60% by weight. Reactor composition can be monitored by subjecting periodically taken samples to gas chromatographic analysis. With suitable agitation of the reaction mixture (e.g., mechanical stirring with an input of from 50 to 500 W/m$^3$ and preferably from 75 to 425 W/m$^3$), reaction proceeds at a highly satisfactory rate under the foregoing conditions. Thus reaction periods in the range of two to three hours will often suffice. Upon completion of the reaction, the reaction mixture will typically contain in the range of 8 to 12% by weight of dimer and at least 52% by weight of trimer.

A preferred embodiment of this invention involves feeding the above amount of the alcohol catalyst promoter portionwise into the reactor containing the monoolefin and the pressurized atmosphere of boron trifluoride as the oligomerization reaction proceeds. Such portionwise feed can be conducted by feeding portions of the total alcohol charge as a series of individual increments over a period of time. In this case the alcohol is caused to enter the system as a discontinuous series of small additions until the preselected amount to be used pursuant to this invention has been introduced into the oligomerization mixture. Alternatively, and preferably, the feed of the alcohol to the oligomerization mixture is conducted slowly and continuously until the total amount of the alcohol has been added. In either case the alcohol feed rates should be from 0.8 to 4 parts by weight of alcohol per 1000 parts of olefin per hour, preferably from 1 to 3 parts by weight of alcohol per 1000 parts of olefin per hour, and most preferably from 2 to 2.6 parts by weight of alcohol per 1000 parts of olefin per hour.

A further important advantage of this invention is the fact that the consumption of boron trifluoride and additionally, the amount of boron trifluoride-containing waste products from the process are both minimized.

Not only does reduced boron trifluoride consumption improve the economic viability of the process by reducing raw material costs but in addition, the substantial costs associated with safe and proper disposal of boron trifluoride-containing waste products such as the dihydrate of boron trifluoride are reduced.

The linear monoolefins used in the process are preferably vinyl olefins ranging from 1-hexene to 1-eicosene. The vinyl olefin is either a straight chain olefin (no branching) or a remotely-branched olefin such that the terminal double bond is unhindered sterically. Mixtures of such monoolefins can also be used. However, such mixtures should be devoid of internal or vinylidene olefins. Preferred linear monoolefins are those having from 8 to 12 carbon atoms. The most preferred monoolefin is 1-decene.

Alcohol promoters that can be used include alkanols having up to about 18 carbon atoms, and preferably up to about 12 carbon atoms, such as, for example, ethanol, 2-propanol, n-butanol, 2-methylpropanol, n-hexanol, n-heptanol, n-octanol, 2-ethylhexanol and n-decanol. More preferably, the alcohol used has up to 6 carbon atoms. The most preferred alcohol is n-butanol. Diols and other polyols can be used, but are less preferred.

Temperatures used in the process are normally in the range of from 20° to 40° C., and preferably from 25° to 35° C.

The boron trifluoride atmosphere within the reactor is typically maintained at a gauge pressure within the range of 2 to 4 bars including 1 bar of nitrogen. A preferred pressure range is from 2.5 to 3.5 bars gauge with 1 bar (gauge) of nitrogen.

The total quantities of olefin and alcohol promoter in the requisite proportions can be charged to the reactor at the outset. However, as noted above, it is preferable to feed the alcohol promoter into the reactor portionwise as the reaction is proceeding, commencing at about the start of the oligomerization. By introducing the alcohol to the reaction mixture in this manner, increased dimer and trimer yields are ensured even though operating at the high olefin conversions of this invention.

To discontinue the oligomerization reaction when the preselected olefin conversion has been achieved, the reaction mixture can be drenched with water. Unreacted olefin can be recovered and recycled to an ensuing reaction.

The following non-limiting example illustrates the practice and advantages of this invention.

EXAMPLE

Oligomerization of 1-decene is conducted using 0.42 mol % of n-butanol based on the 1-decene charged. The butanol is charged at a continuous rate equivalent to 2.3 g per 1000 g per hour. The reactor headspace is maintained at approximately 3 bar pressure with approximately 1 bar of nitrogen. Reaction temperature is maintained at 30° C. After a total time of 145 minutes the reaction is stopped by quenching the product mixture with water. The typical composition of the reaction mixture formed in this manner is as shown in Table I:

TABLE I

| Components | Wt. %, by Gas Chromatography |
|---|---|
| Unreacted monomer | 2 |
| Dimer | 10 |
| Trimer | 57 |
| Tetramer | 22 |
| Pentamer | 8 |
| Hexamer | 1 |

Comparative Example A

When an operation is conducted as described in the example of U.S. Pat. No. 4,950,822 wherein, inter alia, the butanol is used at a concentration of 1.14 mol %, the results were as shown in Table II:

TABLE II

| Components | Wt. %, by Gas Chromatography |
|---|---|
| Unreacted monomer | 1 |
| Dimer | 2 |
| Trimer | 45 |
| Tetramer | 32 |
| Pentamer | 16 |
| Hexamer | 4 |

Comparative Example B

Also for purposes of comparison, when a reaction is conducted as in the above Example of the process of this invention except that the amount of butanol used is from 1.14 to 1.51 mol %, the typical composition of the product is as shown in Table III:

TABLE III

| Components | Wt. %, by Gas Chromatography |
|---|---|
| Unreacted monomer | 0.5 |
| Dimer | 2–3 |
| Trimer | 55–60 |
| Tetramer and higher | Balance |

Upon terminating the oligomerization reaction by quenching the reaction mixture with water or an aqueous solution, an aqueous solution containing boron trifluoride is formed. For ecological and conservational reasons, this aqueous solution is concentrated, typically by distilling off water. The residual aqueous solution contains boron trifluoride dihydrate in solution. As noted above, one of the advantages of this invention is that boron trifluoride consumption can be reduced and this in turn reduces conversion of boron trifluoride to boron trifluoride dihydrate. For example, experimental work has shown that the practice of this invention can reduce boron trifluoride consumption by as much as 50%. A 50% reduction in boron trifluoride utilization in turn translates to a reduction in boron trifluoride dihydrate formation of approximately 50%. Thus instead of forming an amount of boron trifluoride dihydrate equivalent to 1 percent by weight or more based on the weight of vinyl olefin employed, the practice of this invention can result in the formation of less than 0.8 percent by weight, and preferably less than 0.6 percent by weight of boron trifluoride dihydrate based on the weight of vinyl olefin employed.

I claim:

1. A one-stage monoolefin oligomerization process which comprises:

a) contacting in a single stage and in a single reactor a vinyl olefin having in the range of 6 to 20 carbon atoms per molecule with a catalyst comprising boron trifluoride and in the range of from 0.075 to 0.5 mol %, based on the total quantity of olefin being used, of a single alcohol catalyst promoter, at an oligomerization temperature below 40° C. and under a pressurized atmosphere of boron trifluoride in the range of 2 to 4 bars gauge, wherein the alcohol catalyst promoter is introduced portionwise during the course of the oligomerization;

b) monitoring the reactor composition as the reaction proceeds; and c) terminating the reaction when the olefin conversion is at least 95% by weight, the combined total of dimer and trimer in the liquid reaction mixture is at least 60% by weight, and the liquid reaction mixture contains in the range of 8 to 12% by weight of dimer and at least 52% by weight of trimer by quenching the reaction mixture with water or an aqueous solution, and concentrating the resultant aqueous solution containing boron trifluoride to form boron trifluoride dihydrate in solution, wherein the conversion of boron trifluoride to boron trifluoride dihydrate in the solution is equivalent to less than 0.8% by weight based on the weight of vinyl olefin employed in the reaction.

2. A process according to claim 1 wherein the vinyl olefin comprises linear α-monoolefin.

3. A process according to claim 2 wherein the linear α-monoolefin is 1-decene.

4. A process according to claim 1 wherein the temperature is in the range of about 25° to about 35° C.

5. A process according to claim 1 wherein the alcohol promoter is introduced continuously at a rate equivalent to from 1 to 3 parts by weight per 1000 parts by weight of olefin per hour commencing at about the start of the reaction.

6. A process according to claim 1 wherein the alcohol promoter is introduced continuously at a rate equivalent to from 2 to 2.6 parts by weight per 1000 parts of olefin per hour commencing at about the start of the reaction.

7. A process according to claim 6 wherein the alcohol promoter is n-butanol.

8. A process according to claim 1 wherein the reaction period is in the range of two to three hours.

* * * * *